United States Patent
Groteke et al.

(10) Patent No.: US 9,872,657 B2
(45) Date of Patent: *Jan. 23, 2018

(54) VIDEO AND ACCESSORY APPARATUS FOR A VIDEOFLUOROSCOPY UNIT

(71) Applicant: Gleric Holdings, LLC, Clearwater, FL (US)

(72) Inventors: Eric K. Groteke, Houston, TX (US); Glen C. Pettersen, Houston, TX (US)

(73) Assignee: SPINE INJURY SOLUTIONS, INC., Houston, TX (US)

( * ) Notice: Subject to any disclaimer, the term of this patent is extended or adjusted under 35 U.S.C. 154(b) by 278 days.

This patent is subject to a terminal disclaimer.

(21) Appl. No.: 14/736,438

(22) Filed: Jun. 11, 2015

(65) Prior Publication Data
US 2015/0272523 A1 Oct. 1, 2015

Related U.S. Application Data

(63) Continuation of application No. 13/723,372, filed on Dec. 21, 2012, now Pat. No. 9,084,577.

(60) Provisional application No. 61/606,724, filed on Mar. 5, 2012.

(51) Int. Cl.
*A61B 6/00* (2006.01)

(52) U.S. Cl.
CPC .......... *A61B 6/4411* (2013.01); *A61B 6/4417* (2013.01); *A61B 6/4452* (2013.01); *A61B 6/463* (2013.01); *A61B 6/487* (2013.01); *A61B 6/548* (2013.01)

(58) Field of Classification Search
CPC ................. G01N 23/04; G01N 23/223; G01N 2223/076; G01N 2223/301; G01N 2223/308
See application file for complete search history.

(56) References Cited

U.S. PATENT DOCUMENTS

| | | | | |
|---|---|---|---|---|
| 6,088,424 A * | 7/2000 | Postlethwaite | ...... | A61B 6/4441 378/197 |
| 7,806,591 B2 * | 10/2010 | Wang | ...... | A61B 6/00 378/196 |
| 9,084,577 B2 * | 7/2015 | Groteke | ...... | A61B 6/463 |
| 2012/0243667 A1 * | 9/2012 | Walters | ...... | A61B 6/4405 378/206 |

* cited by examiner

Primary Examiner — Hoon Song
(74) Attorney, Agent, or Firm — Keevican Weiss Bauerle & Hirsch LLC; Jeffrey D. Mulrooney

(57) ABSTRACT

A videofluoroscopy accessory device adapted to securely and removably attach to an X-ray head of a fluoroscopy system or device. The videofluoroscopy accessory device on the current invention provides a platform for enhancing and supplementing the surgical environment with additional accessories. The accessories that could be used with the present invention include but are not limited to lights, cameras, microphones, and other medical equipment/tools for optimizing the surgical environment.

23 Claims, 12 Drawing Sheets

VIDEO AND ACCESSORY APPARATUS FOR A VIDEOFLUOROSCOPY UNIT

CROSS-REFERENCE TO RELATED APPLICATIONS

This application is a continuation of patent application Ser. No. 13/723,372, filed Dec. 21, 2012, entitled "Video and Accessory Apparatus for a Videofluoroscopy Unit" which is based on Provisional Patent Application No. 61/606,724, filed Mar. 5, 2012, entitled "Video and Accessory Apparatus for a Videofluoroscopy Unit" and on which priority of this patent application is based, and which are hereby incorporated by reference in their entirety.

BACKGROUND OF THE INVENTION

Field of the Invention

The present invention relates to a videofluoroscopy device. More particularly, it relates to a videofluoroscopy accessory device adapted to securely and removably attach to an X-ray head of a fluoroscopy system or device.

Description of Related Art

Videofluoroscopy devices are known in the prior art and are most commonly used by doctors and practitioners in the fields of chiropractic, orthopedic, osteopathic and sports medicine. The videofluoroscopy device allows a doctor or practitioner to assess problems or abnormalities of a patient's joints, muscles or bones by recording a real time x-ray image of such joints, muscles, and bones on video tape. The video tape can be reviewed at the doctor's or practitioner's leisure, allowing for careful and precise evaluation of a particular problem which might not be evident from an external exam or from conventional static x-ray photos.

Most videofluoroscopy devices are relatively small in design and mount to a wall. The device may be used in an office setting or in a mobile medical vehicle. The videofluoroscopy device mainly consists of a vertical housing enclosing a movement mechanism, the movement mechanism operating a c-arm, the c-arm mounted perpendicularly to a longitudinal axis of the vertical housing and supporting an x-ray device. The movement mechanism directs the c-arm upward and downward along the longitudinal axis of the vertical housing. The x-ray device supported upon the c-arm transmits a real time x-ray image to a video tape recorder thereby recording the movement of the entire body of a patient. In particular, the device records x-ray images of the joints, muscles, and bones and their corresponding movements.

Although videofluoroscopy devices and systems of the prior art have been successful in rending real time x-ray images of individuals, they do not permit the x-ray viewer to simultaneously view the x-ray and a concurrent video image of the patient and/or the concurrent audio of the patient and/or the videofluoroscopy environment. A need exists for doctors and others to simultaneously view the video x-ray with an external image and sounds of a patient. There is also a need for a videofluoroscopy accessory for accomplishing the above and to allow doctors and others to mount lighting, cameras, microphones, and other medical equipment/tools for optimizing the surgical environment.

SUMMARY OF THE INVENTION

Provided herein is a videofluoroscopy accessory device adapted to securely and removably attach to an X-ray head of a fluoroscopy system or device. The videofluoroscopy accessory device on the current invention provides a platform for enhancing and supplementing the surgical environment with additional accessories. The accessories that could be used with the present invention include but are not limited to lights, cameras, microphones, and other medical equipment/tools for optimizing the surgical environment.

The present invention can be particularly helpful for allowing for the positioning of a plurality of video cameras around the surgical field when a fluoroscopy system is being used during surgery. This arrangement allows a surgeon or physician to document and/or view a surgical and/or sterile procedure in a hands free manner, thus aiding in maintaining a sterile surgical environment. The height and angle of the accessories, including video cameras, can be adjusted to allow said accessories to move circumferentially around the sterile field while the present invention is mounted on a fluoroscopy system or device.

It is envisioned that the present invention in one embodiment may comprise a plurality of video cameras, each positioned to view a different angle of a medical procedure where the plurality of views are shown with a view of an X-ray image or an X-ray video on a common visual display. The arrangement has been found to aid users in viewing and perceiving a multi-dimensional environment. For example, a display showing four videos simultaneously of three video camera views from different angles and an X-ray video of the same subject area, a user could see 360 degrees about the subject area and within the area via the X-ray video. Accordingly, a person skilled in the art should appreciate the advantages of the present invention.

In one embodiment the present is a videofluoroscopy accessory for use with a videofluoroscopy device or system, the videofluoroscopy accessory comprises, a clamp adapted to receive an X-ray head of a videofluoroscopy device; at least one accessory mount disposed on the clamp adapted to removably receive at least one predetermined accessory; at least one predetermined accessory; and wherein the at least one predetermined accessory is chosen from a group consisting of a camera, a video camera, a light fixture, a microphone, an image projector, a video projector and an imaging device. In another embodiment, the invention further comprises means for communicating information between said at least one predetermined accessory and the videofluoroscopy device. In yet another embodiment, the invention further comprises an accessory mount arm adapted to connect said at least one predetermined accessory to said clamp. In another embodiment of the invention the circumference of the clamp is adjustable. In still another embodiment of the invention the at least one predetermined accessory comprises at least two video cameras. In yet still another embodiment the invention further comprises means for electrically connecting said at least one predetermined accessory to the videofluoroscopy device. In but another embodiment of the invention, the at least one accessory mount is circumferentially disposed on the clamp. In yet still another embodiment, the at least one of the two video cameras is attached to an accessory mount arm connected to said at least one accessory mount disposed on the clamp.

In another embodiment the invention is a videofluoroscopy accessory for use with a videofluoroscopy device or system, the videofluoroscopy accessory comprising a clamp adapted to receive an X-ray head of a videofluoroscopy device; at least one accessory mount disposed on the clamp adapted to removably receive at least one predetermined accessory; at least one predetermined accessory; at least one accessory mount arm adapted to connect said at least one predetermined accessory to said at least one accessory mount disposed on the clamp; and wherein the at least one predetermined accessory is chosen from a group consisting of a camera, a video camera, a light fixture, a microphone, an image projector, a video projector and an imaging device. In a further embodiment, the invention further comprises means for communicating information between said at least one predetermined accessory and the videofluoroscopy device. In yet another embodiment, the circumference of the clamp is adjustable. In still another embodiment, the at least one predetermined accessory comprises at least two video cameras. In yet still another embodiment, the invention further comprises means for electrically connecting said at least one predetermined accessory to the videofluoroscopy device. In another embodiment, the at least one accessory mount is circumferentially disposed on the clamp. In still another embodiment, the interior circumference of the clamp comprises padding adapted to dampen vibration.

In yet another embodiment, the invention is a videofluoroscopy accessory for use with a videofluoroscopy device or system, the videofluoroscopy accessory comprises a clamp adapted to receive an X-ray head of a videofluoroscopy device; at least one video camera mount disposed on the clamp adapted to removably receive at least one video camera; at least one video camera; at least one video camera mount arm adapted to connect said at least one video camera to said clamp; and wherein the at least one video camera mount and the at least one video camera mount arm are configured to enable selective positioning of the at least one video camera. In another embodiment, the invention further comprises means for communicating information between said at least one video camera and the videofluoroscopy device; and means for electrically connecting said at least one predetermined accessory to the videofluoroscopy device. In still another embodiment, the circumference of the clamp is adjustable. In yet still another embodiment, the at least one video camera mount is circumferentially disposed on the clamp. In but another embodiment, the interior circumference of the clamp comprises padding adapted to dampen vibration.

BRIEF DESCRIPTION OF THE INVENTION

Figure 1:
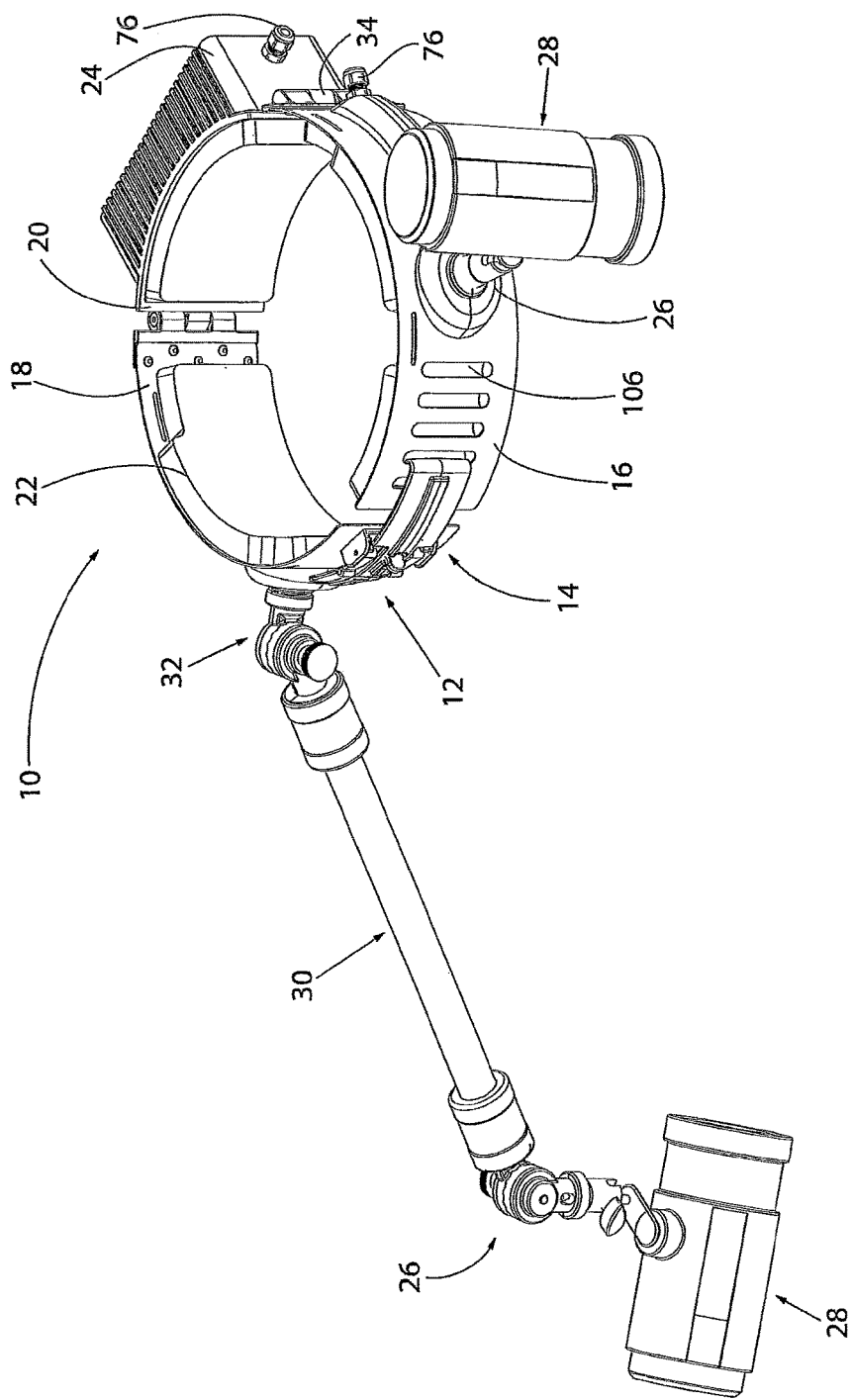
FIG. 1 is a perspective view showing a videofluoroscopy accessory device according to an embodiment of the present invention.
Figure 2:
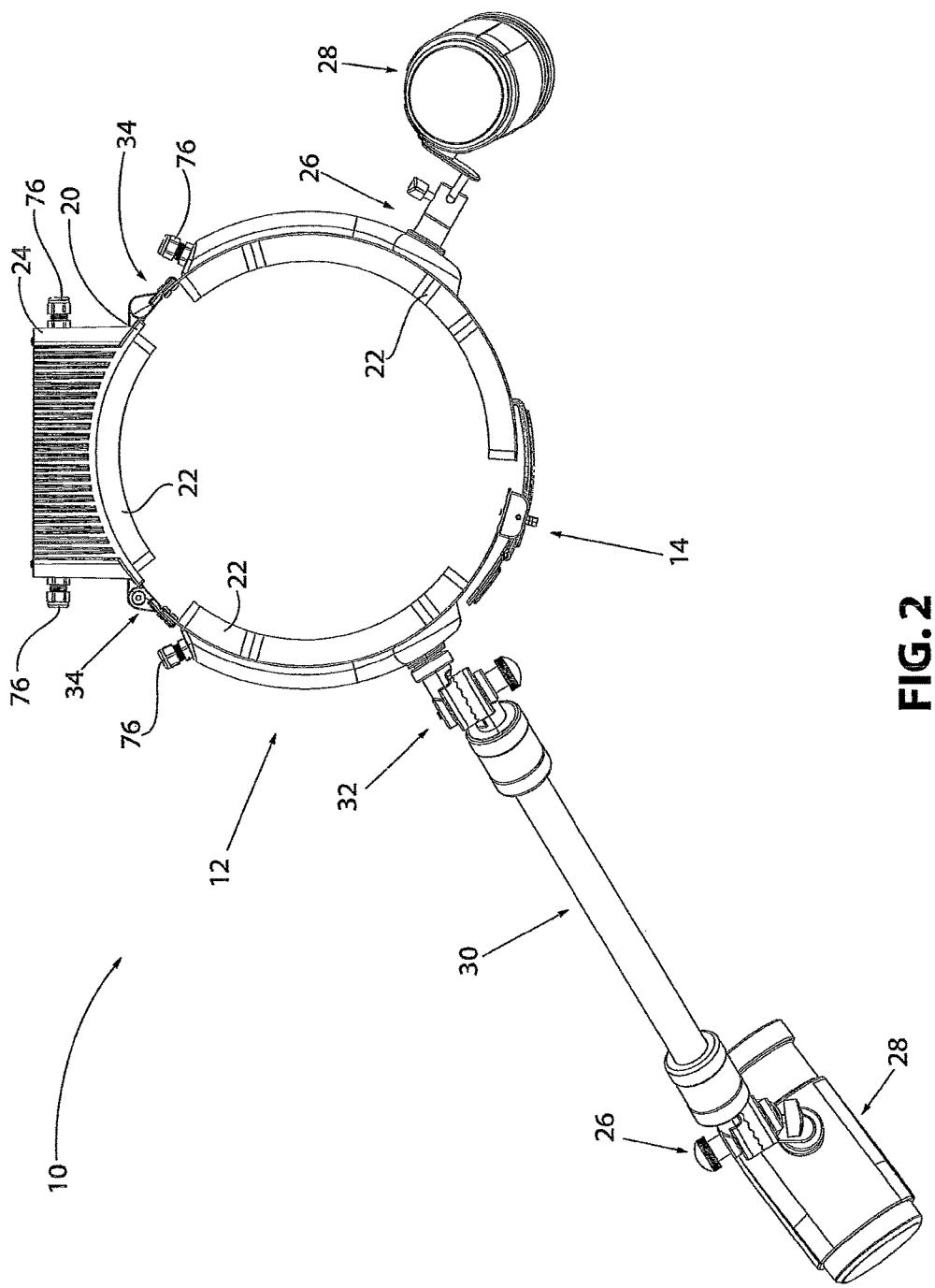
FIG. 2 is a top plan view showing a videofluoroscopy accessory device according to one embodiment of the videofluoroscopy accessory device of FIG. 1.
Figure 3:
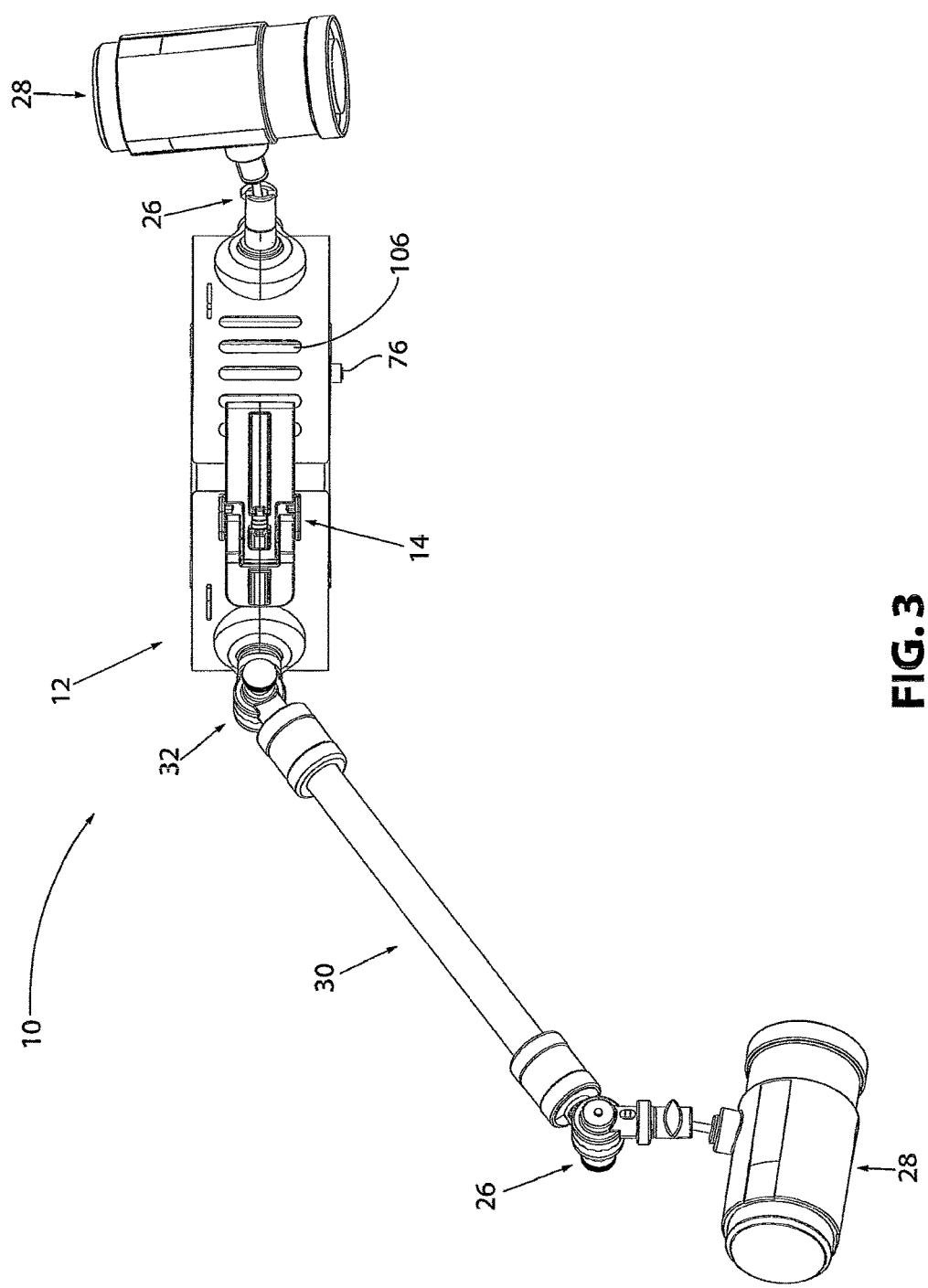
FIG. 3 is a front side elevation view of a videofluoroscopy accessory device according to one embodiment of the videofluoroscopy accessory device of FIG. 1.
Figure 4:
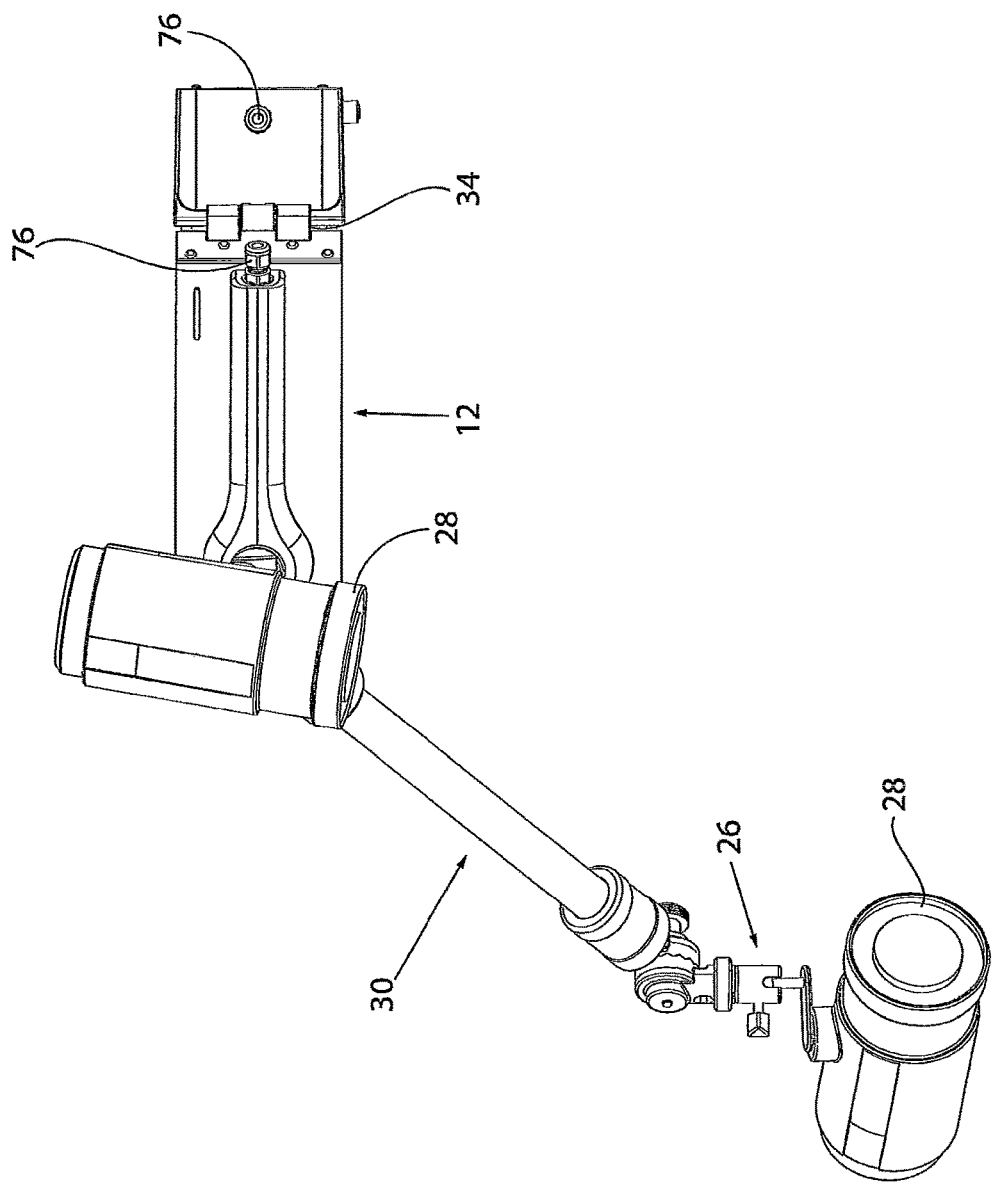
FIG. 4 is a left side elevation view of a videofluoroscopy accessory device according to one embodiment of the videofluoroscopy accessory device of FIG. 1.
Figure 5:
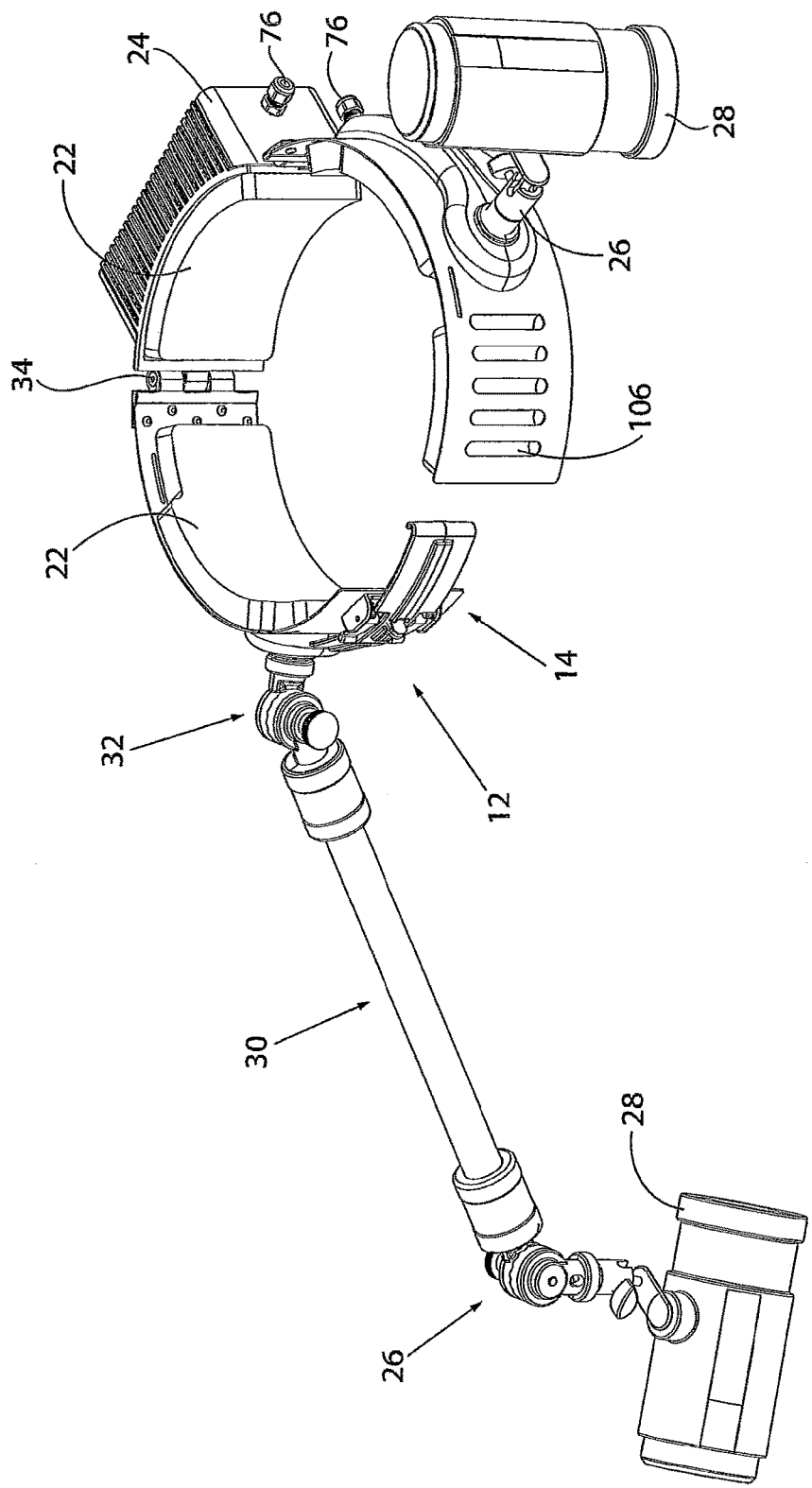
FIG. 5 is a perspective view of a videofluoroscopy accessory device with the clamp in an open position according to one embodiment of the videofluoroscopy accessory device of FIG. 1.

The present invention provides for a videofluoroscopy accessory device adapted to securely and removably attach to an X-ray head of a fluoroscopy system or device. The videofluoroscopy accessory device on the current invention provides a platform for enhancing and supplementing the surgical environment with additional accessories.

These and other features and characteristics of the present invention, as well as the methods of operation and functions of the related elements of structures and the combination of parts and economies of manufacture, will become more apparent upon consideration of the following description with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification, the singular form of "a", "an", and "the" include plural referents unless the context clearly dictates otherwise.

With reference to FIGS. 1-5 and 11-12, presented is a videofluoroscopy accessory device 10. The videofluoroscopy accessory device 10 includes a clamp 12 adapted to engage the periphery of an X-ray head 110 of a fluoroscopy system or other X-ray head. The clamp 12 could be a band clamp, or any suitable clamp capable of being secured to an X-ray head 110. X-ray heads are produced in a variety of sizes and shapes and accordingly the clamp 12 should be constructed to fit the applicable X-ray head. X-ray heads are typically cylindrical or cuboidal in shape but could be constructed with almost any shape.

The clamp 12 may further include a closure 14, a left perimeter section 16, a right perimeter section 18, and a back perimeter section 20. The perimeter sections are connected by hinges 34 and are closed together by closure 14. The left perimeter section 16, the right perimeter section 18, and the back perimeter section 20 may have padding 22 or some vibration damping material disposed on the inside perimeter of the clamp 12 to reduce vibration between the x-ray head and the videofluoroscopy accessory device 10. The padding 22 could also be adapted to provide improved fit and securement to the X-ray head 110. The clamp 12, particularly left perimeter section 16, right perimeter section 18, and back perimeter section 20, may be constructed of a rigid, semi-rigid, flexible material or a combination thereof.

The clamp 12 may further include an electrical enclosure 24 for containing any desired electrical components. It is envisioned that the electrical enclosure 24 could contain power and communication means for powering any accessories and providing communication between the accessories and a videofluoroscopy system or the like. For example, the power and communication means could comprise a networking switch, a circuit board, a power over Ethernet (POE) system or device, a wireless communication system, a battery, a power supply, a fuse, a breaker, a microprocessor, a power isolation system or the like.

The clamp 12 further includes at least one accessory mount 26 for mounting an accessory, such as, video camera 28. The clamp 12 may also include an arm mount 32 for attaching an accessory mount arm 30 and an accessory mount 26 to the clamp 12.

Figure 6:
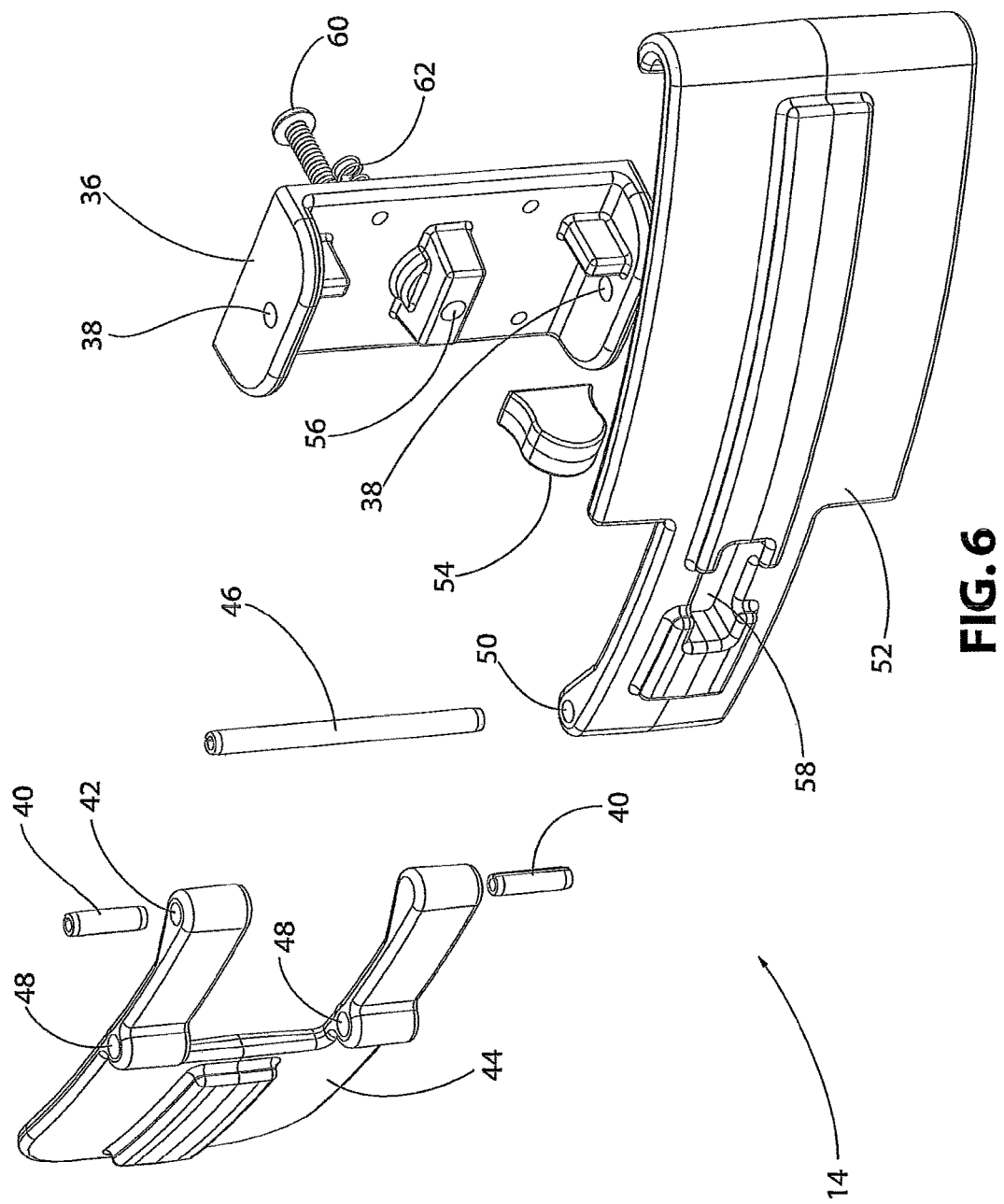
FIG. 6 is a close up exploded view the parts of the clamp closure according to one embodiment of the videofluoroscopy accessory device of FIG. 1.

Now referencing FIG. 6, the closure 14 comprises a bracket 36 for connecting the closure to the clamp 12. Apertures 38 in bracket 36 receives short pins 40 and short pins 40 are received in apertures 42 of paddle 44. Long pin 46 is received in apertures 48 of the paddle 44 and aperture 50 of hook member 52. Rotatable tab 54 is rotatably connected to bracket 36 at connection 56. Rotatable tab 54 is configured to be received in tab hole 58 and to lock the closure closed when rotated in tab hole 58. The bracket 36 may be secured to clamp 12 by means of screw 60 and spring 62 disposed on the bracket 36.

Now referencing FIGS. 1, 3, 5-6 and 11-12, hook member 52 of closure 14 is configured to engage a plurality of slots 106 in the left perimeter section 16 of the clamp 12.

Figure 7:
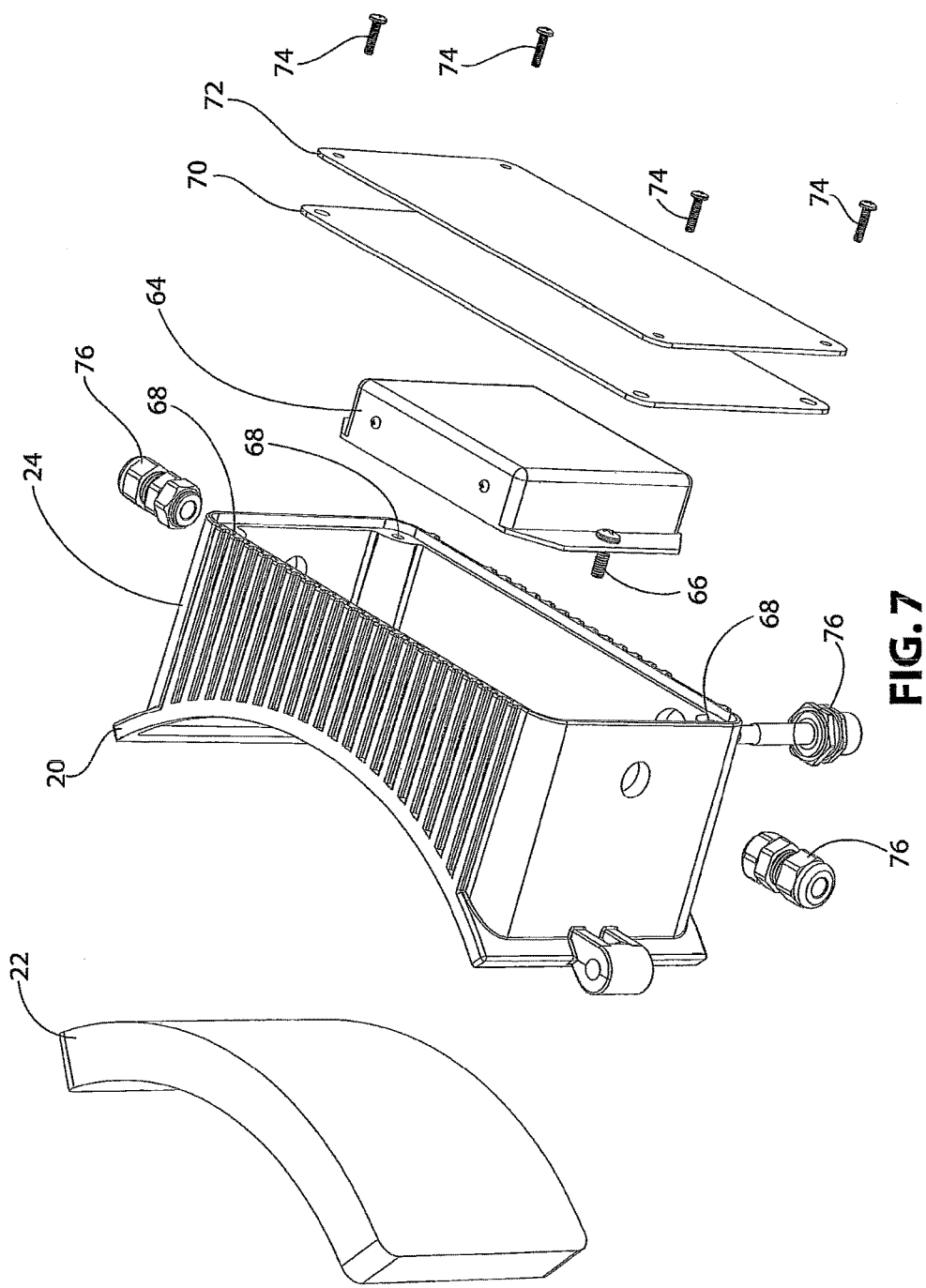
FIG. 7 is a close up exploded view showing the parts that make up the electrical enclosure according to one embodiment of the videofluoroscopy accessory device of FIG. 1.

Now referencing FIG. 7, the electrical enclosure 24 and back perimeter section 20 may be integrally formed as shown or could be separately formed. As discussed above padding 22 may be attached to the clamp 12 to dampen vibrations or assist in forming a secure attachment to an X-ray head. The electrical enclosure 24 may include sub-enclosure 64 which could be attached by means of screws 66 to the inside of electrical enclosure 24. The sub-enclosure may be transparent or transluceint and contain a light source for indicating that the videofluoroscopy accessory device 10 is powered on or to indicate some other status of the device. Screw holes 68 are provided in order to secure first face plate 70 and second face plate 72 to the electrical enclosure 24 by means of screws 74. The electrical enclosure 24 may also include electrical connectors 76 for routing wires or cables to any desired accessory.

Figure 8:
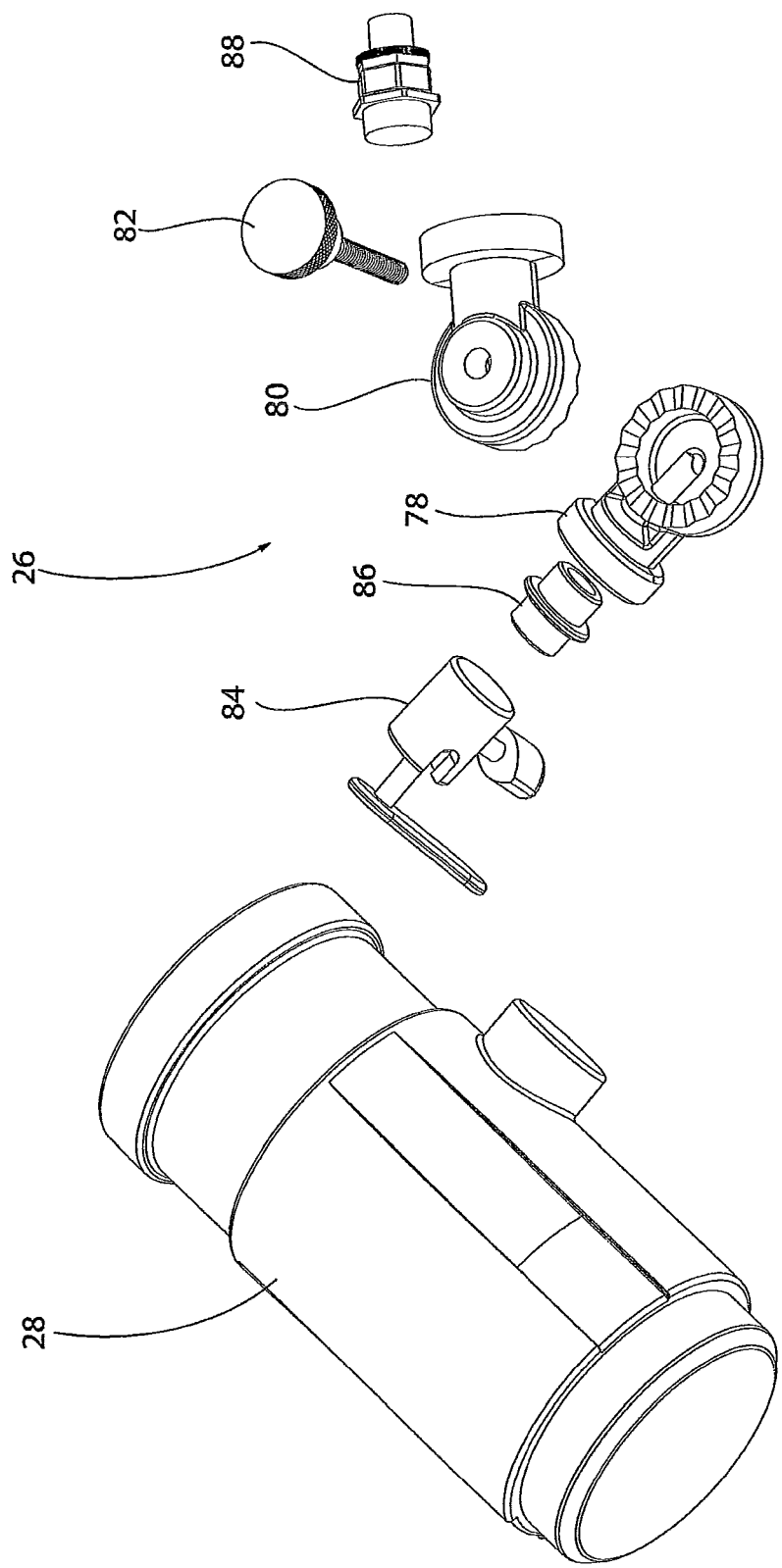
FIG. 8 is a close-up exploded view of a camera mount and a video camera according to one embodiment of the videofluoroscopy accessory device of FIG. 1.

Now referencing FIG. 8, the accessory mount 26 may include first rotatable joint element 78 and second rotatable joint element 80 joined by hand screw 82, which are joined to rotatable mount 84 by means of connector 86. The accessory mount 26 may the be connected to the clamp 23 or the accessory mount arm 30 by connector 88 The accessory mount 26 could be any suitable adjustable camera mount or other mount for attaching an accessory. Preferably the accessory mount can be selectively positioned so that the accessory can face any direction. This can be accomplished with suitable lockable ball and socket joint or a combination joint that includes a plurality of rotatabable joints arranged so that the accessory can be oriented in any direction. It is also envisioned that the accessory mount could be motorized and remotely operable.

Figure 9:
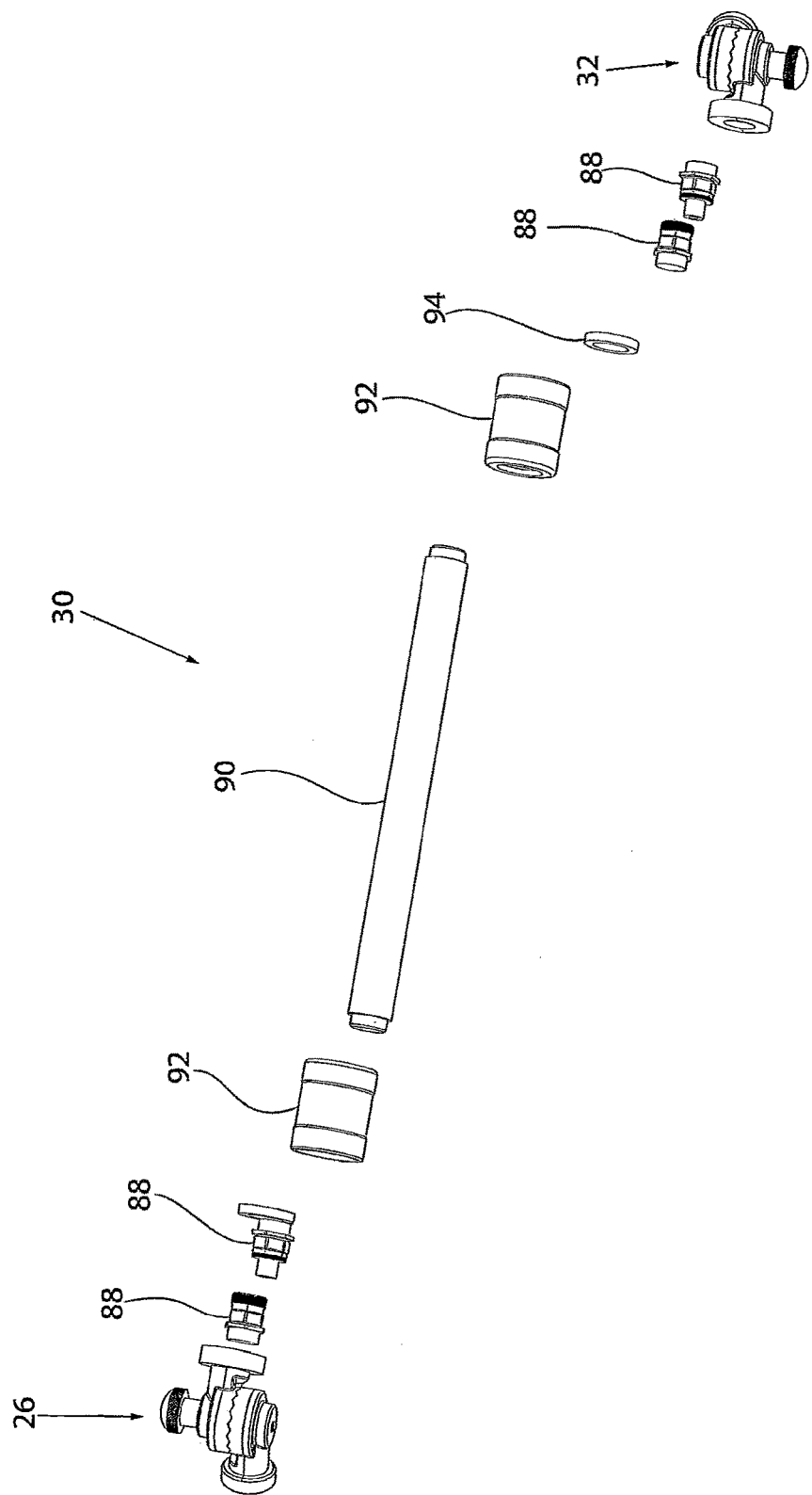
FIG. 9 is an exploded view of an accessory mount arm according to one embodiment of the videofluoroscopy accessory device of FIG. 1.

Now referencing FIG. 9, the accessory mount arm 30 may include arm 90 with couplings 92 which may be connected to accessory mount 26 and/or arm mount 32 by means of connectors 88 and washer 94. The accessory mount arm 30 may be hollow and may have a channel or course inside to house wiring or cabling for connecting accessories to the electrical enclosure 24.

Figure 10:
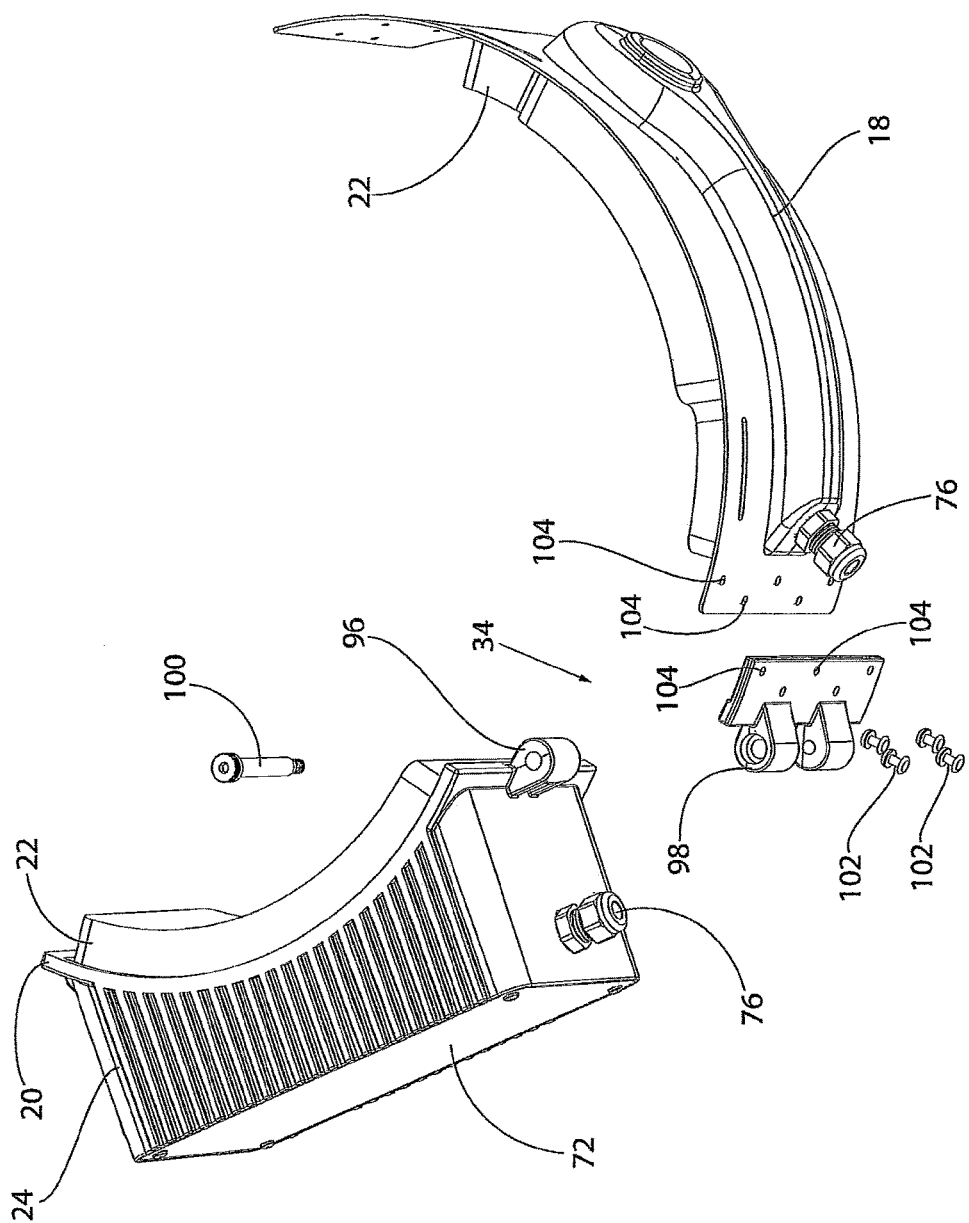
FIG. 10 is a partial exploded view of a hinge for connecting the electrical enclosure portion to the right side portion of the videofluoroscopy accessory device according to one embodiment of the videofluoroscopy accessory device of FIG. 1.
Figure 11:
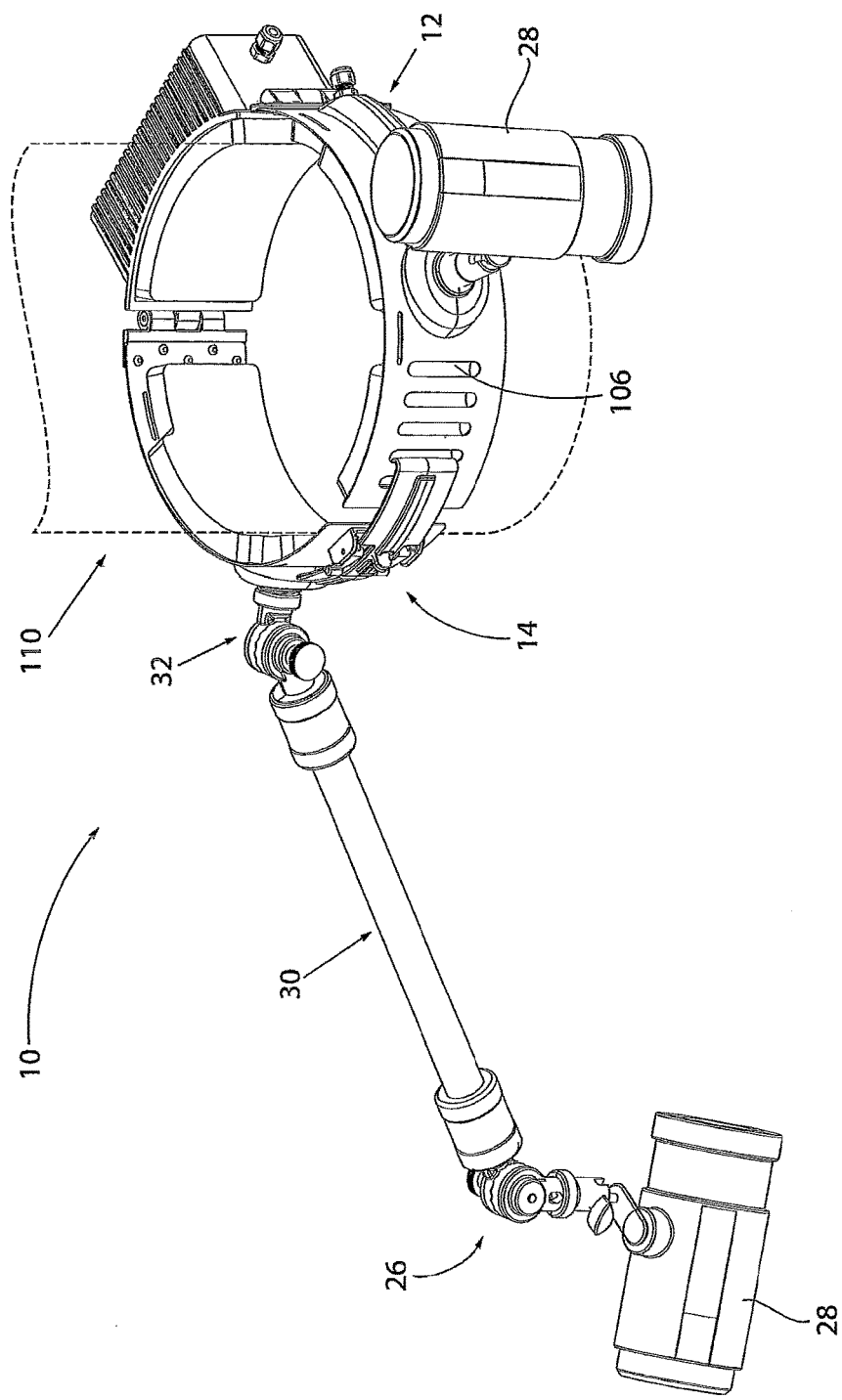
FIG. 11 is a perspective view showing a videofluoroscopy accessory device fitted to an X-ray head of a fluoroscopy system according to one embodiment of the videofluoroscopy accessory device of FIG. 1.
Figure 12:
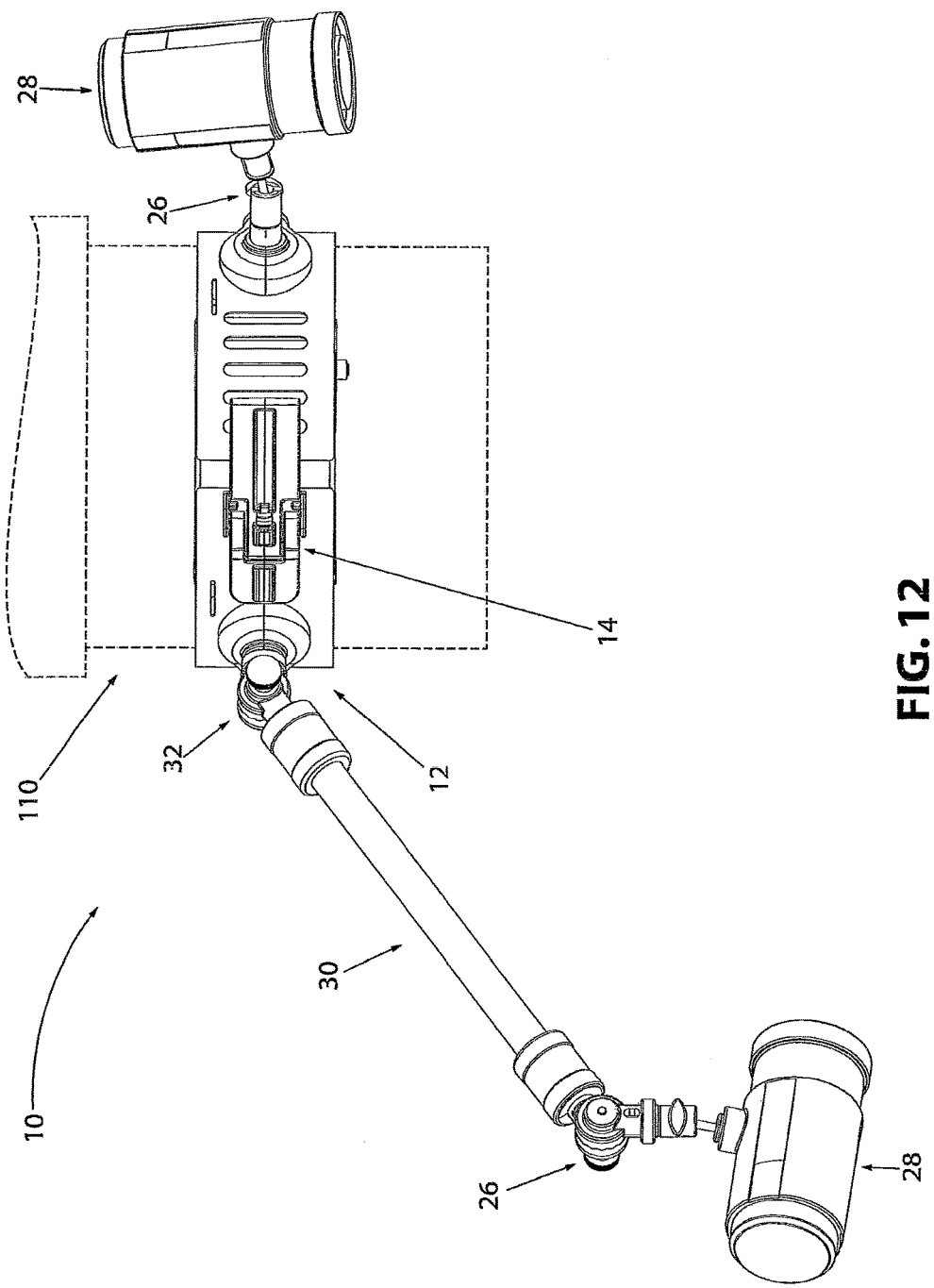
FIG. 12 is a front side elevation view of a videofluoroscopy accessory device fitted to an X-ray head of a fluoroscopy system according to one embodiment of the videofluoroscopy accessory device of FIG. 1.

Now referencing FIG. 10, the right perimeter section 18 and the back perimeter section 20 may be hingedly connected to each other by hinge 34. Hinge 34 may comprise first barrel 96, second barrel 98 and pin 100 for connecting both barrels to each other. The first barrel 96 may be integrally formed with back perimeter section 20. The hinge 34 may then be connected to right perimeter section 18 by fastening fasteners 102 through holes 104.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A videofluoroscopy accessory for use with a videofluoroscopy device or system, the videofluoroscopy accessory comprising:
   a clamp adapted to receive an X-ray head of a videofluoroscopy device,
   at least one accessory mount disposed on the clamp adapted to removably receive at least one predetermined accessory,
   at least one predetermined accessory,
   wherein the clamp is a ring clamp configured to encircle the X-ray head of the videofluoroscopy device, and
   wherein the at least one predetermined accessory is chosen from a group consisting of a camera, a video camera, a light fixture, a microphone, an image projector, a video projector and an imaging device.

2. The videofluoroscopy accessory according to claim 1, further comprising means for communicating information between the at least one predetermined accessory and the videofluoroscopy device.

3. The videofluoroscopy accessory according to claim 1, further comprising an accessory mount arm adapted to connect the at least one predetermined accessory to the clamp.

4. The videofluoroscopy accessory according to claim 1, wherein the circumference of the clamp is adjustable.

5. The videofluoroscopy accessory according to claim 1, further comprising an accessory mount arm adapted to connect the at least one predetermined accessory to the clamp, wherein the accessory mount arm defines a hollow channel for housing a wire or a cable.

6. The videofluoroscopy accessory according to claim 1, further comprising means for electrically connecting the at least one predetermined accessory to the videofluoroscopy device.

7. The videofluoroscopy accessory according to claim 1, further comprising an accessory mount arm adapted to connect the at least one predetermined accessory to the clamp, wherein the accessory mount arm defines a hollow channel for housing a wire or a cable, and
   further comprising means for electrically connecting the at least one predetermined accessory to the videofluoroscopy device.

8. The videofluoroscopy accessory according to claim 1, further comprising means for communicating information between the at least one predetermined accessory and the videofluoroscopy device, an accessory mount arm adapted to connect the at least one predetermined accessory to the clamp, and
    wherein the accessory mount arm defines a hollow channel for housing at least part of the means for communicating information between the at least one predetermined accessory and the videofluoroscopy device.

9. A videofluoroscopy accessory for use with a videofluoroscopy device or system, the videofluoroscopy accessory comprising:
    a clamp adapted to receive an X-ray head of a videofluoroscopy device,
    at least one accessory mount circumferentially disposed on the clamp adapted to removably receive at least one predetermined accessory,
    at least one predetermined accessory,
    at least one accessory mount arm adapted to connect the at least one predetermined accessory to the at least one accessory mount disposed on the clamp,
    wherein the clamp is a ring clamp configured to encircle the X-ray head of the videofluoroscopy device, and
    wherein the at least one predetermined accessory is chosen from a group consisting of a camera, a video camera, a light fixture, a microphone, an image projector, a video projector and an imaging device.

10. The videofluoroscopy accessory according to claim 9, further comprising means for communicating information between the at least one predetermined accessory and the videofluoroscopy device.

11. The videofluoroscopy accessory according to claim 9, wherein the circumference of the clamp is adjustable.

12. The videofluoroscopy accessory according to claim 9, wherein the at least one accessory mount arm defines a hollow channel for housing a wire or a cable.

13. The videofluoroscopy accessory according to claim 9, further comprising means for electrically connecting the at least one predetermined accessory to the videofluoroscopy device.

14. The videofluoroscopy accessory according to claim 9, further comprising means for communicating information between the at least one predetermined accessory and the videofluoroscopy device, and
    wherein the at least one accessory mount arm defines a hollow channel for housing at least part of the means for communicating information between the at least one predetermined accessory and the videofluoroscopy device.

15. The videofluoroscopy accessory according to claim 9, further comprising a wire or a cable for communicating information between the at least one predetermined accessory and the videofluoroscopy device, and
    wherein the at least one accessory mount arm defines a hollow channel for housing at least part of the wire or the cable for communicating information between the at least one predetermined accessory and the videofluoroscopy device.

16. The videofluoroscopy accessory according to claim 9, wherein the at least one accessory mount can be selectively positioned so that the accessory can face any direction.

17. The videofluoroscopy accessory according to claim 9, wherein the at least one accessory mount is motorized and remotely operable.

18. A videofluoroscopy accessory for use with a videofluoroscopy device or system, the videofluoroscopy accessory comprising:
    a clamp adapted to receive an X-ray head of a videofluoroscopy device,
    at least one video camera mount disposed on the clamp adapted to removably receive at least one video camera,
    at least one video camera mount arm adapted to connect the at least one video camera to the clamp,
    wherein the clamp is a ring clamp configured to encircle the X-ray head of the videofluoroscopy device, and
    wherein the at least one video camera mount and the at least one video camera mount arm are configured to enable selective positioning of the at least one video camera.

19. The videofluoroscopy accessory according to claim 18, further comprising means for communicating information between the at least one video camera and the videofluoroscopy device, and means for electrically connecting the at least one predetermined accessory to the videofluoroscopy device.

20. The videofluoroscopy accessory according to claim 18, wherein the circumference of the clamp is adjustable.

21. The videofluoroscopy accessory according to claim 18, wherein the at least one video camera mount attn defines a hollow channel for housing a wire or a cable.

22. The videofluoroscopy accessory according to claim 18, further comprising means for communicating information between the at least one video camera and the videofluoroscopy device, the at least one video camera mount arm adapted to connect the at least one video camera to the clamp, and
    wherein the at least one video camera mount arm defines a hollow channel for housing at least part of the means for communicating information between the at least one video camera and the videofluoroscopy device.

23. The videofluoroscopy accessory according to claim 18, further comprising an electrical enclosure attached to the clamp,
    wherein the electrical enclosure comprises electrical connectors for routing wires or cables to the at least one video camera.

* * * * *